United States Patent [19]

Favre

[11] 4,275,299

[45] Jun. 23, 1981

[54] METHOD AND APPARATUS FOR DETECTING A FLUORESCENT AREA ON A SHEET OF PAPER

[75] Inventor: Nicolas Favre, Cornaux, Switzerland

[73] Assignee: Compagnie Industrielle Radioelectrique, Switzerland

[21] Appl. No.: 30,819

[22] Filed: Apr. 17, 1979

[30] Foreign Application Priority Data

Apr. 18, 1978 [CH] Switzerland ............... 4131/78

[51] Int. Cl.³ ............... G06K 7/10; G01N 21/38
[52] U.S. Cl. ............... 250/271; 250/252; 250/461 R
[58] Field of Search ............... 250/461 R, 372, 461 B, 250/252, 459, 365, 271; 235/468, 491

[56] References Cited

U.S. PATENT DOCUMENTS

| | | | |
|---|---|---|---|
| 3,444,517 | 5/1969 | Rabinow | 250/271 |
| 3,614,430 | 10/1971 | Berler | 250/271 |
| 3,736,428 | 5/1973 | Monroe | 250/372 |
| 3,751,667 | 8/1973 | Quittner | 250/372 |
| 3,854,050 | 12/1975 | Peterson et al. | 250/461 B |
| 3,918,812 | 11/1975 | Holm | 250/461 B |
| 3,935,922 | 2/1976 | Cooper et al. | 250/461 R |
| 4,158,778 | 6/1979 | Gard et al. | 250/461 R |

*Primary Examiner*—Alfred E. Smith
*Assistant Examiner*—Carolyn E. Fields
*Attorney, Agent, or Firm*—Robert E. Burns; Emmanuel J. Lobato; Bruce L. Adams

[57] ABSTRACT

Method for the detection, on a sheet of paper, of an area which becomes fluorescent when it is exposed to ultraviolet radiation, in which the paper sheet passing in front of a detector is illuminated by means of a source of ultraviolet light modulated by a frequency of between 1 and 10 KHz. The modulated fluorescent radiation is detected, amplified and demodulated by means of an amplification circuit and a demodulation circuit providing a first signal. The intensity of the ultraviolet source is measured by a photo-electric member associated with a detection and demodulation circuit supplying a second signal. This second signal is used to regulate the level of operation of at least one trigger which operates to provide an output, corresponding to the fluorescent radiation, when the level of the first signal supplied to the trigger is at at least the trigger operating level.

3 Claims, 2 Drawing Figures

METHOD AND APPARATUS FOR DETECTING A FLUORESCENT AREA ON A SHEET OF PAPER

FIELD OF THE INVENTION

This invention relates to a method and apparatus for detection, on a moving sheet of paper, of an area which becomes fluorescent when it is exposed to ultraviolet radiation, according to which the sheet moving in front of a detector is illuminated by means of a source of ultraviolet light and the fluorescent radiation is detected by means of a photo-electric member.

The method is intended in particular for the authentification of certificates or other documents provided with printed marks or marks applied manually with an ink which has the property of becoming fluorescent under ultraviolet illumination.

BACKGROUND OF THE INVENTION

U.S. Pat. No. 2,950,799 describes filtering ultraviolet light, placing a polarising screen and band-pass filter in front of the photo-electric cell detecting the fluorescent radiation. The current measured is amplified and applied to a galvanometer provided with a contact. However, despite the polarisation and filtering of the fluorescent radiation, daylight or light coming from an artificial source using gas may influence the photo-electric detection cell by reflection and diffusion of the light in the violet range of the spectrum. Furthermore, detection errors may occur on account of a variation in the intensity of the ultraviolet source, for example when the lamp is changed, the intensity of spectral rays for the same supply current varying from one lamp to another and on account of the considerable ageing to which known spectral lamps are subject.

SUMMARY OF THE INVENTION

An object of the invention is to obviate or at least mitigate these drawbacks, by providing a method capable of being used to ensure correct detection independent of foreign sources of light and variations in the intensity of the ultraviolet source.

According to a first aspect of the invention there is provided a method for the detection, on a sheet of paper, of an area which becomes fluorescent when it is exposed to ultraviolet light, comprising passing the sheet in front of a detector comprising a photo-electric member detecting fluorescent radiation from the sheet illuminated by ultraviolet light from a source of ultraviolet light modulated by a frequency of at least approximately 1 KHz., amplifying and demodulating the detected modulated fluorescent radiation, measuring the intensity of the ultraviolet source, and using this measurement to regulate the level of an output signal corresponding to the fluorescent radiation.

In a particular embodiment the source of ultraviolet light is modulated by a frequency of between approximately 1 KHz and 10 KHz.

The value of 10 KHz for the modulation frequency is a maximum value imposed by the characteristics of spectral mercury lamps known hitherto, but a modulation frequency greater than 10 KHz may be envisaged in the case where a spectral lamp would allow such a modulation.

The modulation of the ultraviolet light results in a modulation of the fluorescent radiation and a modulation of the current passing through the photoelectric member. It is henceforth sufficient to filter, detect and demodulate the signal corresponding to the variation in this current in order to obtain the useful signal, the parasite radiation picked-up by the photo-electric member producing either a continuous or quasi-continuous signal or a signal modulated to the mains frequency, i.e. 50 Hz, these parasite signals being eliminated by the detector.

According to a second aspect of the invention there is provided apparatus for detecting, on a moving sheet of paper, an area which becomes fluorescent when it is exposed to ultraviolet radiation, comprising a source of ultraviolet light, means for filtering this ultraviolet light, means for filtering the fluorescent radiation, a first photoelectric member sensitive to the fluorescent radiation, a circuit for processing a first signal derived from the current passing through the photo-electric member, a source of current modulated by a frequency of at least approximately 1 KHz. for supplying the ultraviolet source, a circuit for the detection and demodulation of the current passing through the photo-electric member receiving the fluorescent radiation, a second photo-electric member located in front of a ultraviolet source for detecting radiation therefrom after filtering, said second photo-electric member being associated with a circuit for detection and demodulation supplying a second signal, and at least one trigger controlled by the first signal, the operating level of said trigger being regulated by the second signal.

BRIEF DESCRIPTION OF DRAWINGS

Each aspect of the invention will now be described, by way of example, with reference to the accompanying drawings, in which.

DESCRIPTION OF PREFERRED EMBODIMENT

Figure 1:
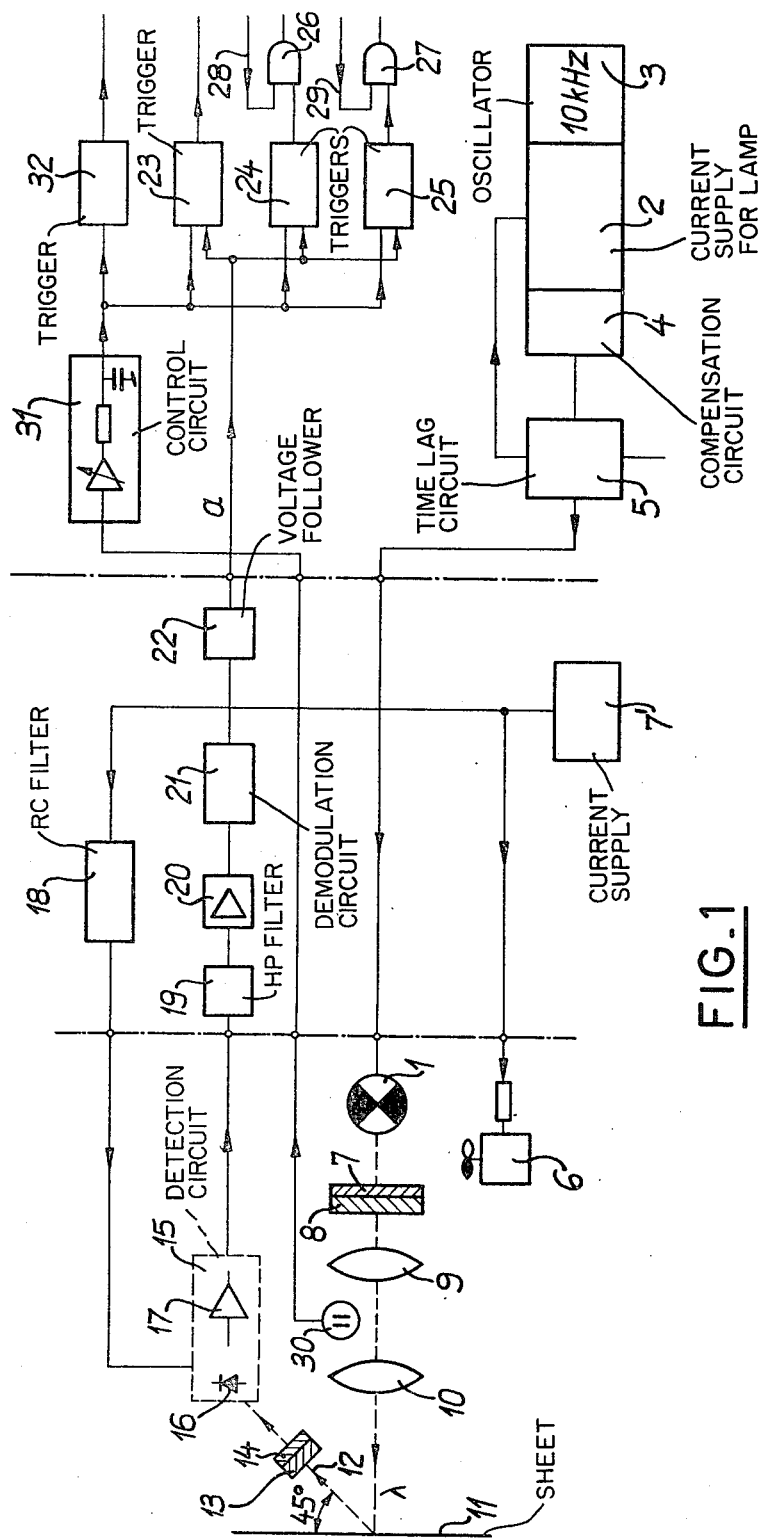
FIG. 1 in a block diagram of apparatus formed according to the second aspect for carrying out the method according to the first aspect of the invention.

With reference to the drawings, the apparatus comprises a source of ultraviolet light 1 constituted by a mercury vapour spectral lamp. This lamp is supplied by a supply source 2 constituted by a commercial ELGAR (Kontron) supply source modulated by an oscillator 3 at a frequency of 10 KHz. The current of the spectral lamp is stabilised by means of a self-induction coil connected in series. In order not to have an excessively inductive charge, since the supply source cannot operate with such a low cos ψ, the latter is raised by means of a compensation circuit 4. Since the spectral lamp 1 cannot be re-illuminated directly when it is hot, a time-lag circuit 5 has been incorporated. The lamp is cooled by a fan 6 supplied by a supply source 7'. The light from the lamp 1 is filtered by means of two filters 7 and 8 in order to obtain approximately monochromatic radiation (wave length predetermined for the fluorescent element). The filter 7 absorbs infrared rays. The filtered rays are focussed by means of two biconvex lenses 9 and 10. The focussed radiation strikes the sheet 11 to be checked. The fluorescent radiation 12 produced when the focussed radiation strikes a fluorescent mark on the sheet is filtered by means of a band-pass filter 13,14 (band predetermined for the fluorescent element).

The means for detecting the fluorescent radiation essentially comprise a detection circuit 14 composed of a "operational amplifier silicon voltage HUV-1000 B EG and G" cell. This circuit comprises a photo-sensitive cell 16 constituted by a photodiode connected with reverse polarisation in order to have information proportional to the light intensity. This photodiode is associated with an operational amplifier 17 connected in the same box as the photodiode 16. The cell 15 is supplied by the supply source 7' through an RC filter 18. The signal provided by the detection cell 15 is filtered by a high-pass filter 19 composed of an RC cell whose cut-off frequency is approximately 20 KHz. The filtered signal is amplified by an amplifier 20 constituted by three stages, each stage using a National LM 318H amplifier. The filtered signal is demodulated by means of a demodulation circuit 21 similar to the demodulation circuit appearing in FIG. 2, which will be described hereafter. The demodulation circuit 21 is followed by a voltage follower stage 22 making it possible to obtain a low output impedance. The output signal is applied to three triggers 23, 24 and 25. The trigger 23 is used to calibrate the lamp. The signal supplied by the trigger 24 is applied to a first AND-gate 26 in order to supply a signal corresponding to the detection of a first fluorescent mark, whereas the signal coming from the trigger 25 is applied to a second AND-gate 27 representing a maximum level of fluorescence. There is applied to the AND-gate 26 a signal 28 determining a reading window corresponding to the area of the sheet 11 in which the mark made with fluorescent ink is to be found. There is applied to the AND-gate 27 a signal 29 determining a reading window corresponding to the presence of a sheet 11 in front of the detector. These reading windows are generated in manner known per se by means of an angular coder kinematically connected to the drums driving the machine and supplying pulses at a frequency of 10 KHz. The length of one period corresponds to a predetermined movement of the sheet 11, for example 0.562 mm. The reading windows make it possible to limit reading in the areas to be checked and thus reduce the danger of errors and prevent the detection of signals which are correct but appear in incorrect areas.

From one lamp to another, the intensity of the spectral rays for the same supply current is not constant. On the other hand, known spectral lamps are subject to considerable ageing. In order to take these variations into account, the reference level of the triggers 23 to 25 is varied according to the variations in illumination of the lamp 1. To this end, a photo-voltaic solar cell 30 is located in the ultraviolet radiation between the lenses 9 and 10. The current supplied by the solar cell 30 is processed by a circuit 31 illustrated in detail in FIG. 2 and supplying a voltage proportional to the current supplied by the solar cell 30, i.e. to the intensity of the ultraviolet radiation. The output signal of the circuit 31 is applied on the one hand to a fourth trigger 32 supplying a signal making it possible to check the state of the lamp 1 and on the other hand to the three other triggers 23, 24 and 25 for regulating the level of these triggers depending on the intensity of the ultraviolet radiation.

Figure 2:
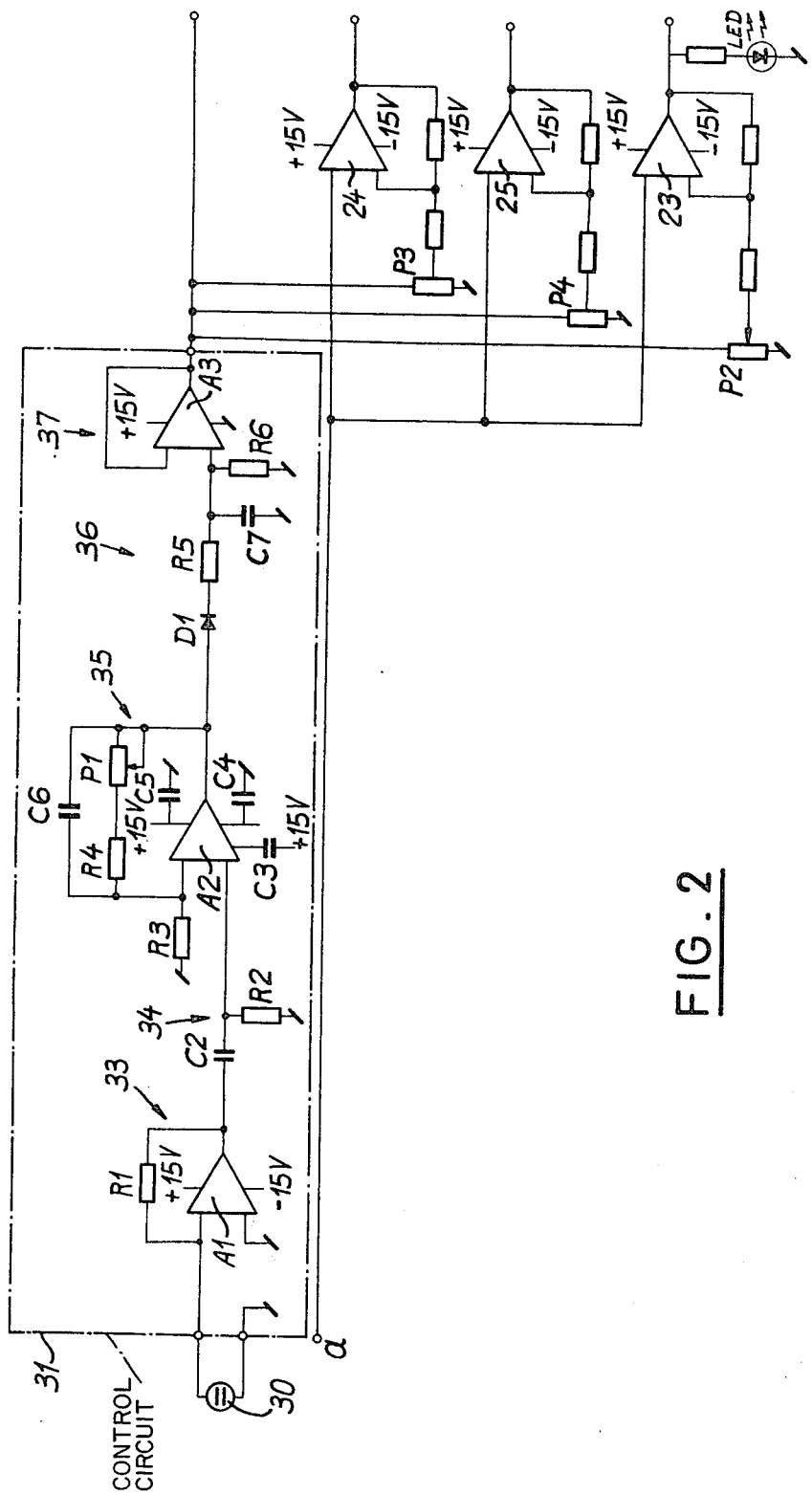
FIG. 2 is a more detailed diagram of the circuit associated in FIG. 1 with the second photo-electric member for controlling the ultraviolet radiation and output circuits.

FIG. 2 shows the circuit associated with the solar cell 30, as well as the three triggers 23, 24 and 25 and their regulating means. The current supplied by the solar cell 30 is converted into a voltage by means of a current-/voltage converter 33 constituted by an operational amplifier A1 and a resistor R1 connected as a regenerative circuit. The signal is then filtered by means of a high-pass filter 34 constituted by a capacitor C2 and a resistor R2. This filter eliminates parasite signals due to the solar light, which result in a continuous signal, as well as the parasite signals due to sources of external light at a frequency of 50 or 60 Hz. The signal is then amplified by means of an amplifier 35 constituted by an operational amplifier A2, two resistors R3 and R4, a potentiometer P1 for adjusting the gain and four capacitors C3, C4, C5 and C6. The capacitor C6 determines the upper cut-off frequency. The signal modulated to 10 KHz, once amplified, is detected and demodulated by means of a demodulation circuit 36 composed of a diode D1, two resistors R5 and R6 and a capacitor C7. The circuit also comprises a voltage follower stage 37 constituted by an operational amplifier A3 making it possible to obtain a low output impedance for the regulation of the triggers 23, 24 and 25. To this end, the current of the output signal passes through three potentiometers P2, P3 and P4 respectively associated with each of the triggers 23, 24 and 25 and used as voltage dividers for establishing the switching level of these triggers. The current passing through the potentiometers P2, P3, P4 varies as a function of the intensity of the ultraviolet light and the same will be true of the switching level of the triggers. The triggers transform the demodulated analog signal into a digital signal which can be used for controlling the ejection devices.

Each time the spectral lamp 1 is changed, it is necessary to adjust the regulation, since no lamp has the same intensity as a function of the current. In order to do this, one adjusts the gain of the regulation cell by means of a potentiometer P1, in order to obtain the switching point of a LED-diode associated with the trigger 23 and serving as a test lamp.

What is claimed is:

1. Apparatus for detecting on a moving sheet of paper the presence, in predetermined areas, of marks which become fluorescent when exposed to ultraviolet radiation, comprising a source of ultraviolet light, a source of current modulated at a frequency of about 10 KHz for supplying current to said ultraviolet source, first filtering means for filtering ultraviolet light produced by said source and directing said ultraviolet light on said sheet to produce fluorescent radiation from said marks, second filtering means for filtering said fluorescent radiation from said marks, a first photo-electric element sensitive to fluorescent radiation and disposed on the same side of said sheet as said source of ultraviolet radiation to receive filtered fluorescent radiation from said marks to produce a first-signal, first circuit means for detecting, demodulating and amplifying said first signal received from said first photo-electric element, a second photo-electric element disposed between said first filtering means and said sheet to receive directly ultraviolet light from said source filtered by said first filtering means to produce a second signal, second circuit means for detecting, demodulating and amplifying said second signal, means coordinated with movement of said sheet to produce first and second reading windows, first trigger means controlled by said first signal and said first reading window producing means to produce a first output signal measured on a first predetermined area of the sheet, second trigger means controlled by said first signal and said second reading window producing means to produce a second output signal measured on a second predetermined area of the sheet, and means controlled by said second signal for regulating the operating level of both of said trigger means.

2. Apparatus according to claim 1, in which said second circuit means comprises a potentiometer for adjusting the gain of said second circuit means, further comprising third trigger means responsive to said first signal and regulated by said second signal, and a test lamp energized by said third trigger means for determining adjustment of gain by said potentiometer.

3. Apparatus according to claim 2, further comprising fourth trigger means controlled solely by said second signal and supplying a third output signal for checking said ultraviolet source.

* * * * *